United States Patent [19]

Ray

[11] Patent Number: 5,055,104
[45] Date of Patent: Oct. 8, 1991

[54] SURGICALLY IMPLANTING THREADED FUSION CAGES BETWEEN ADJACENT LOW-BACK VERTEBRAE BY AN ANTERIOR APPROACH

[75] Inventor: Charles D. Ray, Deephaven, Minn.

[73] Assignee: Surgical Dynamics, Inc., Alameda, Calif.

[21] Appl. No.: 432,087

[22] Filed: Nov. 6, 1989

Related U.S. Application Data

[63] Continuation-in-part of Ser. No. 259,031, Oct. 17, 1988, Pat. No. 4,961,740.

[51] Int. Cl.$^5$ ............................ A61F 5/04; A61F 2/44
[52] U.S. Cl. ............................................ 606/61; 623/17
[58] Field of Search .................... 606/53, 60, 61, 72, 606/73; 623/16, 17; 128/69; 267/162, 166, 168, 289, 290

[56] References Cited

U.S. PATENT DOCUMENTS

| | | | |
|---|---|---|---|
| 190,061 | 4/1877 | Middleton | 267/290 |
| 200,860 | 3/1878 | French | 267/290 |
| 1,418,758 | 6/1922 | Watkins | 267/289 |
| 1,486,295 | 3/1924 | Mullen | 267/290 |
| 1,905,498 | 4/1933 | Pfeiffer | 267/290 |
| 3,880,414 | 4/1975 | Smith | 267/168 |
| 4,309,777 | 1/1982 | Patil | 606/61 |
| 4,820,305 | 4/1989 | Harms | 606/61 |
| 4,901,987 | 2/1990 | Greenhill | 267/166 |
| 5,349,921 | 9/2982 | Kuntz | 623/17 |

FOREIGN PATENT DOCUMENTS 1222260 4/1986 U.S.S.R. ................ 606/60

Primary Examiner—Mickey Yu
Assistant Examiner—Michael Brown
Attorney, Agent, or Firm—Fliesler, Dubb, Meyer & Lovejoy

[57] ABSTRACT

When an intervertebral fusion is required, and the disc space is unusualy large, that disc space can be preserved by surgically implanting a pair of relatively large male-thread fusion cages 20, 20A with their threads 13 overlapping. Because of their large size, such fusion cages 20, 20A should be implanted by an anterior approach to the lower back. When each of the cages is made of a shape-retaining helix 22 of wire that is hollow within the helix 22 and has openings 23 between adjacent turns, the cages 20, 20A can be removed after the adjacent vertebrae have become fused together and without disrupting that fusion, thus guarding against possible rejection of the cages 20, 20A by the patient's body. The anterior approach and scaled-down fusion cages 20, 20A may be used in cervical spine fusions.

20 Claims, 3 Drawing Sheets

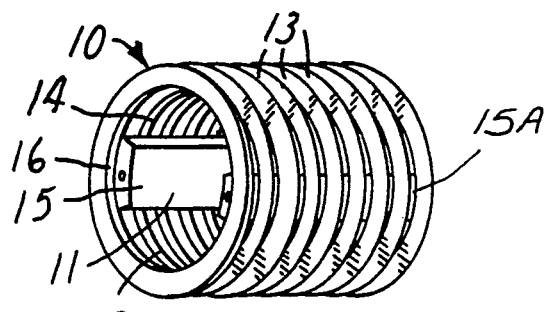
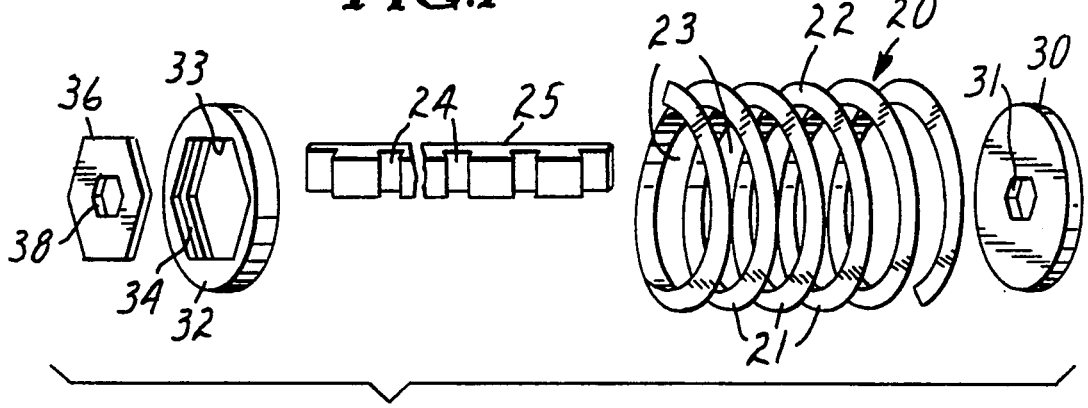
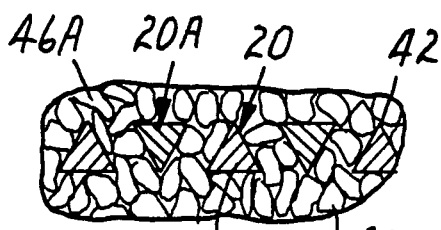
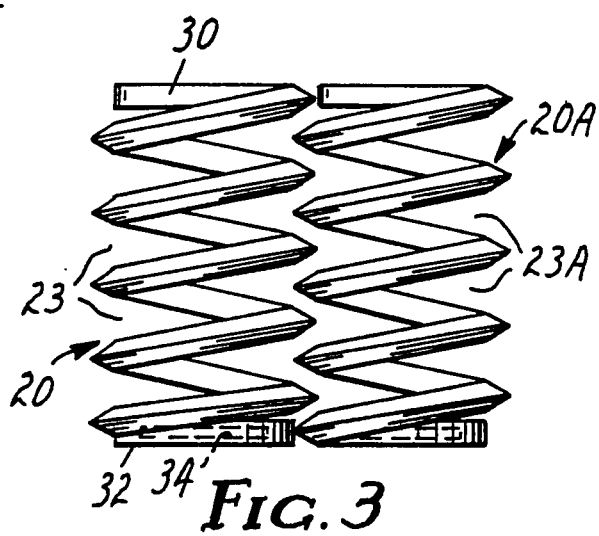
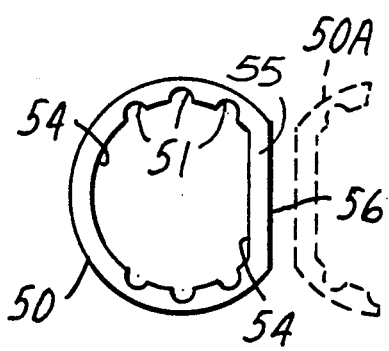
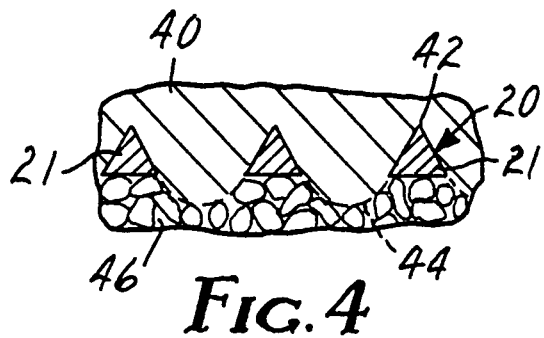

SURGICALLY IMPLANTING THREADED FUSION CAGES BETWEEN ADJACENT LOW-BACK VERTEBRAE BY AN ANTERIOR APPROACH

CROSS-REFERENCE TO RELATED APPLICATIONS

This is a continuation-in-part of copending U.S. Pat. No. b 4,961,740 issued Oct. 9, 1990 and entitled "V-THREAD FUSION CAGE AND METHOD OF FUSING A BONE JOINT". The present application also is related to an application entitled "SURGICAL METHOD AND APPARATUS FOR FUSING ADJACENT BONE STRUCTURES" assigned U.S. Pat. application Ser. No. 07/432,088 and filed on Nov. 6, 1989.

BACKGROUND OF THE INVENTION

1. Field of the Invention

The invention concerns method and apparatus for fusing two adjacent vertebrae of the lower spine by an anterior approach and also concerns V-thread and other male-thread fusion cages that are specially adapted for situations requiring the anterior approach.

2. Description of Related Art

Prior art fusion devices such as described above are not suitable for the requirements for which the present invention has been developed.

U.S. Pat. No. 4,501,269 (Bagby) describes a surgical procedure for stabilizing the cervical spine of a horse and says that the procedure is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint. The process was developed to immediately stabilize the joint and to further promote ultimate bone-to-bone fusion . . . . The implanted structure is in the form of a perforated cylindrical bone basket which can be filled with bone fragments produced during the preparation of the joint. These bone fragments provide autogenous tissue to promote bone growth through the basket, as well as around it.

The process involves the initial steps of surgically accessing the joint and removing intervening cartilage located between the contiguous bony surfaces. A transverse cylindrical opening is then bored across the contiguous bony surfaces. Immediate stabilization is achieved by driving into the cylindrical opening a hollow basket having a rigid perforated cylindrical wall whose outside diameter is slightly greater than the inside diameter of the cylindrical opening. The implanting of the basket spreads the bony surfaces apart in opposition to the resistance to expansion of the joint provided by the surrounding ligaments (col. 2, lines 26–55).

U.S. Pat. No. 2,537,070 (Longfellow) shows in FIG. 2 a "reinforce 7" that is much like Bagby's fusion basket.

Vich, J. Neurosurg., Vol 63, pp 750–753 (1983) describes a means for cervical spine fusion, using an anterior approach, by surgically implanting a cylindrical bone graft.

"Screw threads are placed in the graft with a small, previously sterilized die. The grooves of the thread can be made as deep as required. The vertebral cervical bodies are prepared according to Cloward's technique. After a cylindrical bed has been drilled in the appropriate intervertebral bodies, the graft is screwed into place with instruments especially developed for this purpose" (p. 750). Vich's FIG. 2 legend points out that a threaded graft dowel has a larger contact surface than a plain dowel and a greater resistance to pressure and sliding. Vich also says:

"When grafts with a diameter of 14 mm were used, we sometimes threaded the receiving bed with a die-stock of 13 mm to facilitate the insertion" (p. 751).

SUMMARY OF THE INVENTION

Prior art fusion devices such as described above are not suitable for the requirements for which the present invention has been developed.

A large majority of patients requiring intervertebral fusion have narrowing of the disc space, typically 10 mm or less in the lower back. Because minimal penetration (about 3 mm) into the end plates of the vertebrae is required three major diameters of the male thread of the fusion cage should suffice for most patients, namely, 14, 16 and 18 mm. Anatomical problems arise when the vertical height of the disc space is much greater than 10 mm, because that height should be preserved to control disabling pain on motion of the diseased disc. The vertical disc space may be as great as about 14 mm which would require a pair of male-thread fusion cages of about 20 mm outside diameter for appropriate bivertebral penetration. The spinal canal is not wide enough, the distances between adjacent bony anatomical structures are too short, and the nerve and dura cannot be retracted far enough medially to safely clear the drilling and tapping procedures for posterior implantation of such large male-thread fusion cages.

Because vertebrae of the lower back of an adult are roughly oval in cross section and about 30 to 35 mm deep by 45 to 50 mm wide and because the male-thread fusion cages should be about 25 mm in length to afford good fore-and-aft stability, the largest rectangular space safely available for the cages is about 25 mm deep and 35 mm wide. If the fusion cages were to protrude from the vertebral oval, they could contact major blood vessels or nerves lying close to both the anterior and posterior aspects of the vertebral bodies. To guard against this, the parallel axes of threaded bores to receive 20-mm cages should be less than 16 mm apart in order to keep the cages safely within the vertebral oval.

When the bores overlap, the bit used in drilling the second bore has a tendency to drift toward a common center. The bit also tends to wander because the consistency of cancellous bone of the vertebral bodies is similar to wet balsa wood while that of the hard shell is similar to about a 1.5 mm veneer of white oak.

The present invention answers the above-outlined problems by an anterior approach to the lower back. The invention also concerns novel male-thread fusion cages and a method of implanting them that allows their threads to overlap, while assuring that the axes of the implanted cages are parallel. The novel male-thread fusion cages resist being forced out of position and toward the center of the disc space due to swelling of tissues lateral to the cages.

One of the novel male-thread fusion cages has the valuable attribute of being removable after the adjacent vertebrae have become fused together, and without disrupting that fusion, thus guarding against possible rejection of the implant by the patient's body. The removable fusion cage is made of a shape-retaining cylindrical helix of wire that is hollow within the helix and has openings between adjacent turns. Those openings preferably are great enough to allow the wire of an identical fusion cage to penetrate to the hollow of the cage when the two cages are side-by-side with their axes parallel. Secured to each end of the helix is a device through which torque can be simultaneously transmitted equally to both ends of the helix, thus permitting it to be inserted into a threaded bore without binding. The torque-transmitting device at the leading end of the fusion cage should not extend, radially outward beyond a circle equal to the inside diameter of the female thread of the bore.

To permit the helix to be removed after the adjacent vertebrae have become fused together, the torque-transmitting device should be so secured to the leading end of the helix that it can come loose simply by screwing the helix outwardly. For example, when both the helix and the torque-transmitting device are metal, they can be tack-welded to separate at the welds.

Upon positioning a pair of these helices in parallel threaded bores between adjacent vertebrae, the side of each helix that faces outwardly in the lateral direction, preferably, should be closed to keep out tissue that could interfere with bone growth between the vertebrae. To do so, an insert can be formed with indentations that snap-fit into the openings between adjacent turns of the helical wire to block the lateral side of the cage that is remote from the other cage.

Preferably, each of the torque-transmitting devices includes means for receiving an end cap for retaining a bone-inducing substance. End caps can also help to prevent disc tissue from growing into the cages. The end caps preferably are X-ray transparent to permit post-operative checks on the status of the developing bone. X-ray transparent end caps can be stamped from a flexible sheet of thermoplastic resin such as "Delrin" acetal resin or polypropylene.

The novel cylindrical helix and two other male-thread fusion cages of the invention are illustrated in the drawing. When the outside diameter of their threads are 20 mm, pairs can be implanted with their parallel axes separated by only about 15 or 16 mm.

As noted above, fusion cages having threads that are 20 mm in diameter should be implanted by an anterior approach to the lower back. The anterior approach, even though safe, is complicated by the need to approach the lower back through the abdomen, usually by passing around and not through the peritoneal sac. Major vessels and autonomic nerves which hug that anterior aspect of the vertebral bodies must be pulled aside. The invention provides a novel template-holding retractor for doing so in a manner which is practical and safe when carefully performed.

THE DRAWING

In the drawing, all figures of which are schematic,

FIG. 1 is an isometric view..of a preferred V-thread fusion cage as disclosed in parent U.S. patent application Ser. No. 07/259,031;

FIG. 2 is an exploded isometric view of a first male-thread fusion cage of the present invention, an insert for blocking one lateral side of the cage, and a pair of end caps;

FIG. 3 shows the side-by-side implanted relationship of a pair of the fusion cages of FIG. 2;

FIG. 4 is a fragmentary cross section of one of the fusion cages of FIG. 2 as it would appear after being implanted between two vertebrae;

FIG. 4A is a fragmentary cross section at the intersection of the pair of the implanted fusion cages of FIG. 2 as they would appear after being implanted between two vertebrae;

FIG. 5 is a cross section through a second male-thread fusion cage of the invention;

DESCRIPTION OF THE PREFERRED EMBODIMENT

Figure 8:
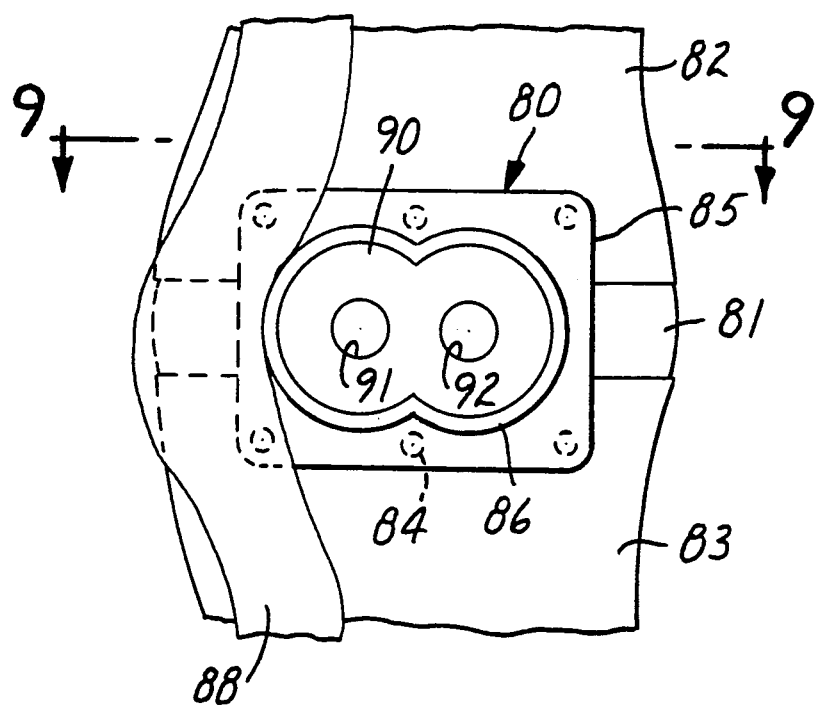
FIG. 8 is an anterior view of a portion of the lower back with a template-holding retractor in place to prepare threaded bores for surgical implantation of a pair of one of the aforementioned male-thread fusion cages.

The fusion cage 10 of FIG. 1 has been formed from a solid metal cylinder by drilling an axial bore 11 and then broaching out a pair of channels 12 that extend to a diameter only a little smaller than the external surface of the cylinder. A V-thread 13 has then been machined in that external surface, thus creating perforations 14 in the valley between adjacent turns of the thread, each perforation extending between a pair of lands 15 and 15A. One land 15, which is wider than the other land 15A, is to be positioned adjacent the edge of the disc to prevent disc tissue from growing into the cage. Each end of each land has been machined to form a recess 16 enabling an end cap (not shown) to fit flush with the end of the fusion cage.

In FIG. 2, a first male-thread fusion cage 20 of the present invention has been formed from triangular wire 21 as a shape-retaining cylindrical helix 22 that has openings 23 between adjacent turns. After the fusion cage 20 and an identical fusion cage 20A have been implanted side-by-side as in FIG. 3, indentations 24 of an insert 25 snap-fit into the openings 23, thus blocking one lateral side of each cage while the unblocked openings 23 at the top and bottom of each helix afford perforations through which bone can grow.

Welded to the leading end of the helix 22 is a first ring 30 that has a small hexagonal opening 31. Welded to the trailing end of the helix 22 is a second ring 32 that has a large hexagonal opening 33. Behind the large hexagonal opening 33 is a slot 34 to receive an end cap 36 that is formed with a small hexagonal opening 38.

To implant the male-thread fusion cage 20 into a bore having a mating thread (not shown), a tool (not shown) simultaneously fits into the hexagonal openings 31 and 33 of the first and second rings 30 and 32, respectively. Rotation of the tool rotates both ends of the helix equally, thus permitting it to be inserted into the threaded bore without binding.

FIG. 3 shows the relationship of the male-thread fusion cage 20 and an identical fusion cage 20A as they would be implanted between adjacent vertebrae in parallel threaded bores, the axes of which are closer together than the outside diameter of each cage. When both of the cages 20 and 20A have been implanted with their helices intermeshing, an insert 25 is snapped into place at the laterally outward side of each helix. Then the hollow within each helix is packed with bone chips, and the trailing end of each fusion cage is closed with an end cap 36. Instead, a single end cap in the form of a figure-8 can close both of the second rings 32 to prevent migration of either cage.

The implanted fusion cage 20 and a vertebra 40 are fragmentally shown in FIG. 4. The crown 42 of the male thread formed by the triangular wire 21 of the fusion cage 20 is sharp, but rounded crowns 44 of the female thread formed in the vertebra 40 protrude into the hollow defined by the inner facing sides 45 of the triangular wire 21 and are contacted by bone chips 46 filling the hollow of the helix.

Referring to FIG. 4A, at the junction between the two fusion cages 20 and 20A, the crown 42 of the triangular wire 21 of each fusion cage penetrates to the hollow of the other cage. Adequate space remains between adjacent turns of the intermeshing helices so that bone chips 46 and 46A within the cages 20 and 20A, respectively, are in contact, thus permitting bone to grow therebetween.

FIG. 5 shows a second male-thread fusion cage 50 of the invention that can be formed from a solid metal cylinder by drilling six small holes 51 in the axial direction, each hole being centered on a circle concentric with the axis of the cylinder. A V-thread (not shown) is machined into the external surface of the cylinder, thus opening perforations through the valley of the V-thread at each crossing with one of the small holes 51. A large hole is drilled on the axis of the cylinder and broached to leave a flat-sided hollow 54 that communicates with said perforations except at the wall 55 at the flat side of the hollow 54. A flat side face 56 at its outer surface gives the wall a uniform thickness. The external V-thread permits the fusion cage 50 and an identical fusion cage 50A (indicated by phantom lines) to be screwed into parallel threaded bores such that the cylinders generated by the crowns of the V-threads of the two cages overlap, thus permitting the two cages to be closer together than would otherwise be feasible.

Figure 6:
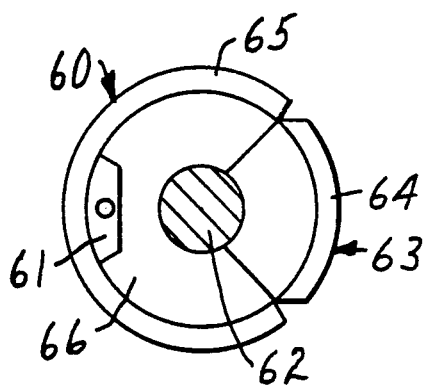
FIG. 6 is an end view of a third male-thread fusion cage of the invention with inserts in place to enable it to be screwed into a threaded bore.

FIG. 6 shows a third male-thread fusion cage 60 that can be made in the same way as the cage 10 of FIG. 1, followed by cutting away one land to produce a C-shaped cross section that has one remaining land 61. The fusion cage 60 can be screwed into a threaded bore by first inserting a rod 62 having a projection 63 that is formed with a thread 64. A C-shaped insert 66 forces the thread 64 to the position shown at which it completes the thread of the fusion cage. The rod 62 protrudes from the wound to permit rotation by a surgeon to implant the fusion cage 60. Then after pulling out the C-shaped insert 66, the projection 63 can be moved centrally for axial removal.

Figure 7:
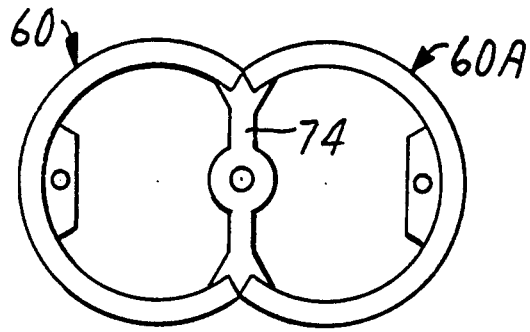
FIG. 7 is an end view of a pair of the fusion cages of FIG. 6 as they would be positioned in parallel threaded bores and interconnected.

After implanting both the fusion cage 60 and an identical fusion cage 60A, they can be interlocked by a septum 74 that slides longitudinally into place as in FIG. 7.

Figure 9:
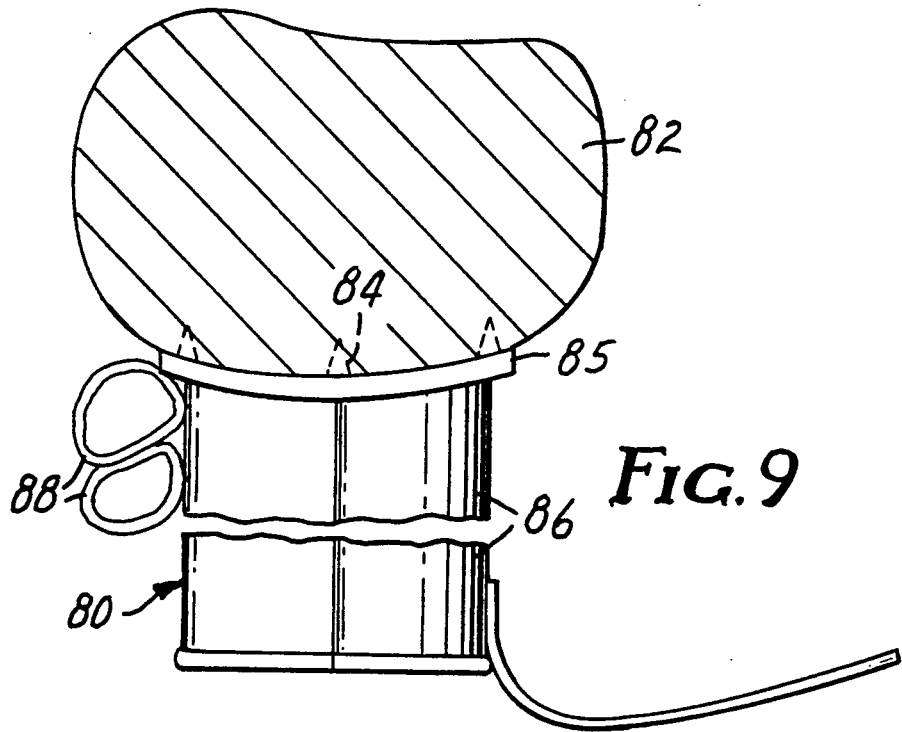
FIG. 9 is a cross section along line 9—9 of FIG. 8.

As shown in FIGS. 8 and 9, a template-holding retractor 80 is useful for preparing threaded bores to permit the anterior implantation of any of the pairs of male-thread fusion cages 20, 50 or 60 into a disc 81 between adjacent vertebrae 82 and 83. The retractor 80 has six spikes 84 that project from a plate 85 and are forced into the cortical shell of both vertebrae after centering the retractor over the disc 81. By doing so, a wall 86 that projects from the opposite face of the plate 85 displaces the great vessels 88 safely to the patient's right side.

The wall 86 has a figure-8 configuration in cross section to receive each of five templates that are shown in FIGS. 8 and 10-13. The first template 90 of FIG. 8 has first and second circular openings 91 and 92 vertically centered over the disc 81 and equally offset to opposite sides of the center of the disc. Each of the circular openings 91 and 92 acts as a guide for a pilot drill.

Figure 10:
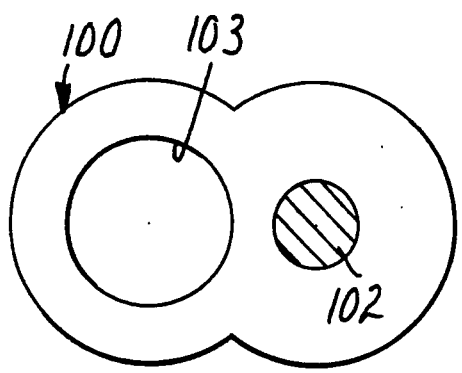
FIGS. 10-13 are plan views of a series of templates to be used with the template-holding retractor of FIGS. 8 and 9.

The second template 100 of FIG. 10 has an index pin 102 which fits into a pilot bore that has been drilled through the second opening 92 of the first template 90 and a circular opening 103 which acts as a guide for enlarging a pilot bore that has been drilled through the first opening 91 of the first template 90. The diameters of the circular opening 103 is selected to ensure that the enlarged bore penetrates through the cortical shells of the vertebrae 81 and 82.

Figure 11:
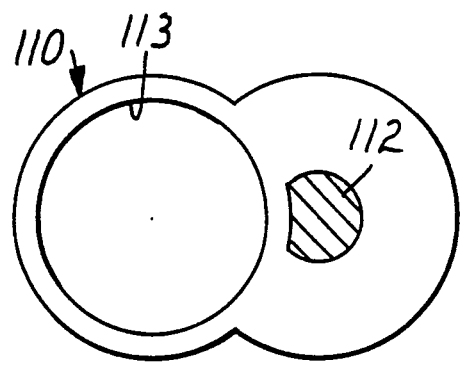

The third template 110 of FIG. 11 has an index pin 112 that fits into a pilot bore that has been drilled through the second opening 92 of the first template and a circular opening 113 that acts as a guide for a tap by which a female thread can be formed in the enlarged bore that has been drilled through the opening 103 of the second template 100. The diameter of the circular opening 113 is selected to ensure that the female thread penetrates into the cancellous bone of each of the vertebrae 81 and 82.

Figure 12:
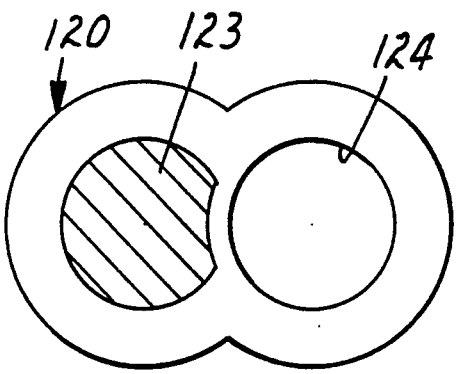

The fourth template 120 of FIG. 12 has an index pin 123 that fits into a bore after it has been threaded through the circular opening 123 of the third template 110. The fourth template also has a circular opening 124 which acts as a guide for enlarging a pilot bore that has been drilled through the second opening 92 of the first template 90. The diameter of the circular opening 124 equals that of the circular opening 103 of the second template.

Figure 13:
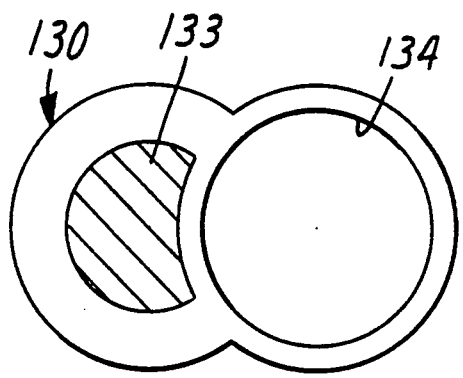

The fifth template 130 of FIG. 13 has an index pin 133 that fits into the same threaded bore as did the pin 123 of the fourth template 120. The fifth template has a circular opening 134 that acts as a guide for the same tap as was inserted through the circular opening 113 of the template 110.

After screwing a pair of male-thread fusion cages into the threaded bores formed using the third and fifth templates 110 and 130 and aligning their imperforate areas (the inserts 25 when implanting cages 20) to be at laterally opposite sides of the pair, each cage is packed with bone chips, and an end cap is inserted Because the illustrated anterior implantation method provides precise positioning of the ends of the pair, a single figure-8 end cap (not shown) can close the trailing ends of both fusion cages. Doing so with a pair of the fusion cages 50 of FIG. 5 provides a desirable lateral stability after implantation, an assurance already achieved when implanting pairs of the fusion cage of FIG. 6 by virtue of the septum 74.

Although the parent U.S. Pat. No. 4,961,704 says that its V-thread fusion cage preferably is made of implantable-grade stainless steel, each of the novel fusion cages is preferably titanium, it having been shown to be more compatible to bone.

The anterior approach and scaled-down fusion cages may be used in cervical spine fusions.

What is claimed is:

1. A fusion cage system for being implanted in and promoting fusion with respect to one of more bone structures, said fusion cage system for containing bone-growth-inducing substance packed therein for accelerating bone fusion, said fusion cage system comprising:
   a first fusion cage which has a first outside dimension and a first internal cavity means for being packed with the bone-growth-induction substance;
   a second fusion cage which has a second outside dimension and a second internal cavity means for being packed with the bone-growth-inducing substance;
   at least one of the first fusion cage and the second fusion cage including means for allowing said first and second fusion cages to be positioned adjacent each other such that an outside dimension of the combination of the first fusion cage positioned adjacent the second fusion cage is less than the sum of the first outside dimension and the second outside dimension.

2. The fusion cage system of claim 1 wherein:
   said first fusion cage and said second fusion cage include first and second means respectively for allowing immediate contact between the one or more bone structures and the bone-growth-inducing substance.

3. The fusion cage system of claim 1 wherein said allowing means includes means for intermeshing the first fusion cage with the second fusion cage.

4. The fusion cage system of claim 1 wherein said allowing means includes means for allowing the first fusion cage to be rotatably implanted and the second fusion cage to be rotatably implanted adjacent the first fusion cage.

5. The fusion cage system of claim 1 including means for blocking a portion of said first fusion cage and a portion of said second fusion cage to prevent tissue ingrowth where blocking occurs.

6. The fusion cage system of claim 1 wherein said allowing means includes a first helical structure formed by the first fusion cage and a second helical structure formed by the second fusion cage.

7. The fusion cage system of claim 6 wherein said first helical structure includes means for intermeshing with the second helical structure.

8. The fusion cage system of claim 1 wherein said first fusion cage includes a first cylindrical body and said allowing means includes a first wall formed along a chord of the first cylindrical body.

9. The fusion cage system of claim 1 wherein said first fusion cage includes a "C"-shaped cylindrical body and said allowing means includes an opening in said "C"-shaped cylindrical body that communicates with said first internal cavity means.

10. A fusion cage system for being implanted in and promoting fusion with respect to one or more bone structures, said fusion cage system for containing bone-growth-inducing substance packed therein for accelerating bone fusion, said fusion cage system comprising:
    a first fusion cage which is substantially cylindrical in shape and which has a first outside diameter and a first internal cavity means for being packed with the bone-growth-inducing substance;
    a second fusion cage which is substantially cylindrical in shape and which has a second outside diameter and a second internal cavity means for being packed with the bone-growth-inducing substance; and
    said second fusion cage including means for allowing said first fusion cage to be rotatably positioned with respect to the one or more bone structures and with respect to the second fusion cage such that the outside dimension of the combination of the first fusion cage positioned adjacent the second fusion cage is less than the sum of the first outside diameter and the second outside diameter.

11. The fusion cage system of claim 10 wherein:
    said first fusion cage and said second fusion cage include first and second means respectively for allowing immediate contact between the one or more bone structures and the bone-growth-inducing substance.

12. A fusion cage system for being implanted in and promoting fusion with respect to one or more bone structures, said fusion cage system for containing bone-growth-inducing substance packed therein for accelerating bone fusion, said fusion cage system comprising:
    a first fusion cage which is substantially cylindrical in shape and which has a first outside diameter and a first internal cavity means for being packed with the bone-growth-inducing substance;
    a second fusion cage which is substantially cylindrical in shape and which has a second outside diameter and a second internal cavity means for being packed with the bone-growth-inducing substance;
    said first fusion cage including first means for allowing the intermeshing of the first fusion cage with the second fusion cage as the second fusion cage is rotatably positioned with respect to the one or more bone structures and with respect to the first fusion cage previously implanted with respect to one or more bone structures; and
    said second fusion cage including second means for allowing the intermeshing of the second fusion cage with the first fusion cage as the second fusion cage is rotatably positioned with respect to the one or more bone structures and with respect to the first fusion cage previously implanted with respect to the one or more bone structures.

13. The fusion cage system of claim 12 wherein:
    said first fusion cage and said second fusion cage include first and second means respectively for allowing immediate contact between the one or more bone structures and the bone-growth-inducing substances.

14. A fusion cage system for being implanted in and promote fusion with respect to one or more bone structures, said fusion cage system for containing bone-growth-inducing substance packed therein for accelerating bone fusion, said fusion cage system comprising:
    a first fusion cage which is comprised of a first helical structure having a first inner surface which defines a first internal cavity, which first helical structure including a plurality of spaced apart first turns, said first helical structure having a first outer diameter;
    a second fusion cage which is comprised of a second helical structure having a second inner surface which defines a second internal cavity, said second helical structure including a plurality of spaced apart second turns, said second helical structure having a second outer diameter;
    wherein the spacing of the first turns and the spacing of the second turns is such that the first turns can intermesh with the second turns when the first fusion cage is implanted beside the second fusion cage with respect to the one or more bone structures, with the overall dimension of the first fusion cage intermeshed with the second fusion cage being less than the sum of the first outer diameter and the second outer diameter.

15. The fusion cage system of claim 14 wherein:
with the first and second fusion cages implanted in the one or more bone structures the spaces between the first turns and the second turns are so configured so that there is immediate contact between the one or more bone structures and the bone-growth-inducing substance packed into the first and second internal cavity.

16. The fusion cage system of claim 14 wherein:
said first turns have first substantially v-shaped outer surfaces pointing in a direction away from the first internal cavity; and
wherein said second turns have second substantially v-shaped outer surfaces pointing in a direction away from the second internal cavity, such that the first and second turns can intermesh in a side-by-side relative to each other, with the first v-shaped outer surfaces of the first turns pointing in opposite directions from the second v-shaped outer surfaces of the second turns at the location of side-by-side intermeshing.

17. The fusion cage system of claim 14 including:
first means for blocking a portion of the space between the first turns at a first location diametrically opposite from where the first turns intermesh with the second turns; and
second means for blocking a portion of the space between the second turns at a second location diametrically opposite from where the second turns intersect with the first turns so as to prevent tissue ingrowth where blocking occurs.

18. The fusion cage system of claim 17 wherein said first blocking means includes means for snapping into the space between the first turns, and the second blocking means includes means for snapping into the space between the second turns.

19. The fusion cage system of claim 14 including means for securing the first helical structure to the second helical structure.

20. The fusion cage system of claim 14 wherein said first fusion cage has a first axis about which said first helical structure is symmetrical and said second fusion cage has a second axis about which said second helical structure is symmetrical, such that with the first turns intermeshed with the second turns and with the first axis and the second axis separated by a distance, the distance is less than the first outer diameter or the second outer diameter.

* * * * *